United States Patent
Saurat

[11] Patent Number: 6,099,528
[45] Date of Patent: Aug. 8, 2000

[54] VERTEBRAL ROD FOR SPINAL OSTEOSYNTHESIS INSTRUMENTATION AND OSTEOSYNTHESIS INSTRUMENTATION, INCLUDING SAID ROD

[75] Inventor: Jean Saurat, Avrille, France

[73] Assignee: Sofamor S.N.C., France

[21] Appl. No.: 09/085,923

[22] Filed: May 28, 1998

[30] Foreign Application Priority Data

May 29, 1997 [FR] France ................................. 97 06621

[51] Int. Cl.$^7$ ................................................. A61B 17/56
[52] U.S. Cl. ............................................. 606/61; 606/53
[58] Field of Search ............................. 606/61, 206, 60, 606/53–56; 600/40, 1

[56] References Cited

U.S. PATENT DOCUMENTS

| | | | |
|---|---|---|---|
| 4,066,073 | 1/1978 | Finney et al. ............................. | 600/40 |
| 4,361,141 | 11/1982 | Tanner ..................................... | 128/69 |
| 4,653,481 | 3/1987 | Howland et al. ........................ | 128/69 |
| 4,697,582 | 10/1987 | William .................................... | 606/61 |
| 4,719,905 | 1/1988 | Steffee .................................... | 128/69 |
| 4,771,767 | 9/1988 | Steffee .................................... | 128/69 |
| 4,815,453 | 3/1989 | Cotrel ..................................... | 128/69 |
| 4,854,304 | 8/1989 | Zielke ..................................... | 128/69 |
| 4,988,357 | 1/1991 | Koss ........................................ | 600/40 |
| 5,067,485 | 11/1991 | Cowen .................................... | 600/40 |
| 5,217,461 | 6/1993 | Asher et al. ............................. | 606/61 |
| 5,281,223 | 1/1994 | Ray ......................................... | 606/61 |
| 5,334,203 | 8/1994 | Wagner ................................... | 606/61 |
| 5,403,314 | 4/1995 | Currier .................................... | 606/61 |
| 5,486,174 | 1/1996 | Fournet-Fayard et al. .............. | 606/61 |
| 5,549,627 | 8/1996 | Kieturakis ................................ | 606/206 |
| 5,591,165 | 1/1997 | Jackson .................................... | 606/61 |
| 5,593,408 | 1/1997 | Gayet et al. ............................. | 606/61 |
| 5,630,816 | 5/1997 | Kambin ................................... | 606/61 |
| 5,658,286 | 8/1997 | Sava ........................................ | 606/61 |
| 5,688,220 | 11/1997 | Verin et al. .............................. | 600/1 |

FOREIGN PATENT DOCUMENTS

| | | | |
|---|---|---|---|
| 2 726 995 | 5/1996 | France ........................... | A61B 17/60 |
| 36 24 067 | 2/1987 | Germany ....................... | A61B 17/60 |
| 2 208 476 | 4/1989 | United Kingdom ........... | A61B 17/56 |

OTHER PUBLICATIONS

Translation of French Patent No. 2 726 995, published May 24, 1996.

*Primary Examiner*—Michael Buiz
*Assistant Examiner*—Jonathan D. Goldberg
*Attorney, Agent, or Firm*—Woodard, Emhardt, Naughton Moriarty & McNett

[57] ABSTRACT

A vertebral rod for fixation of a spine, the rod formed of a first material and defining a passage extending at least partially therethrough, the passage at least partially filled with a second material different from the first material to thereby enable the stiffness of the rod to be varied along its length. The first and second materials are either a metallic material or a biocompatible material such as plastic. The rod may be formed of at least three layers of material, with the layers composed of at least two different materials.

20 Claims, 6 Drawing Sheets

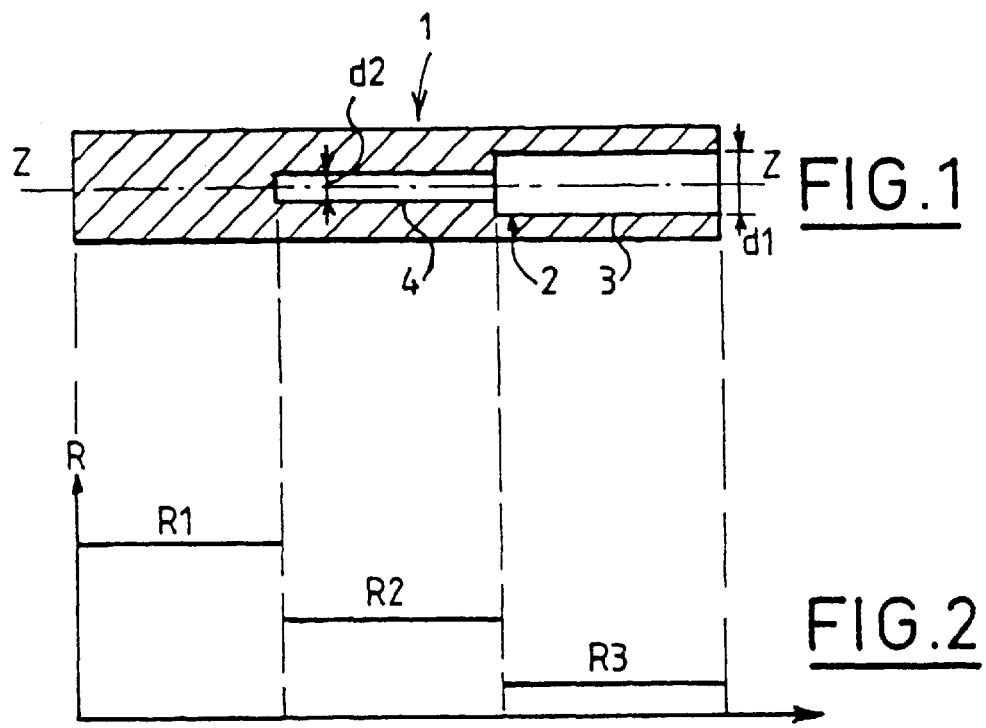
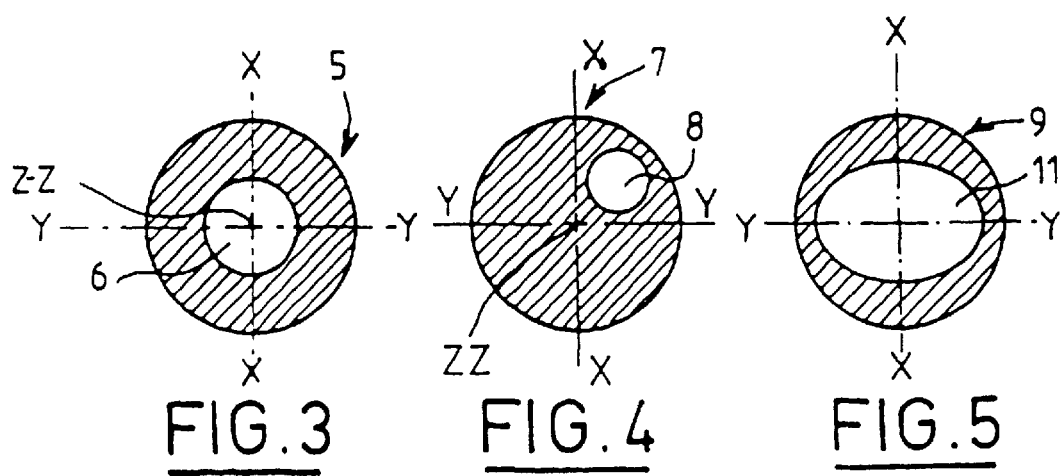

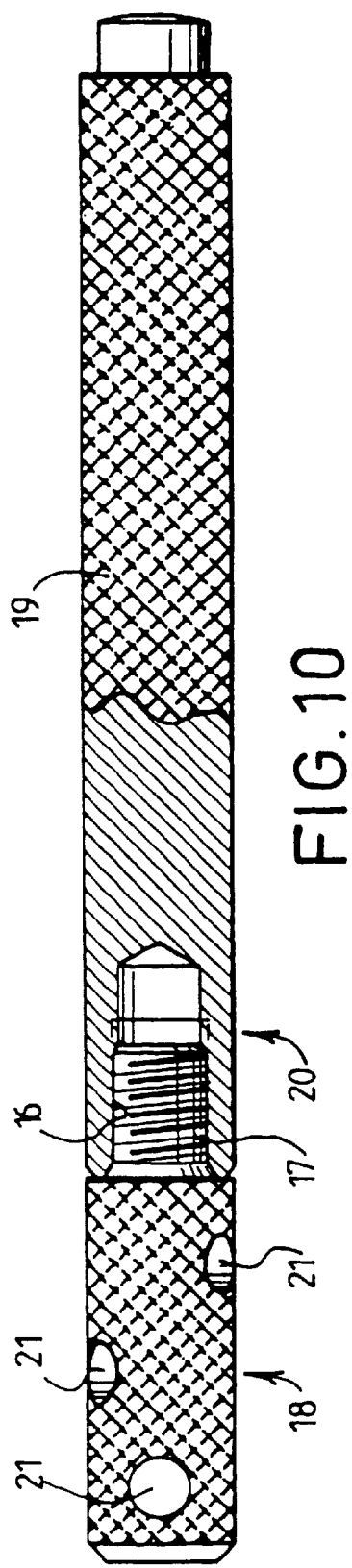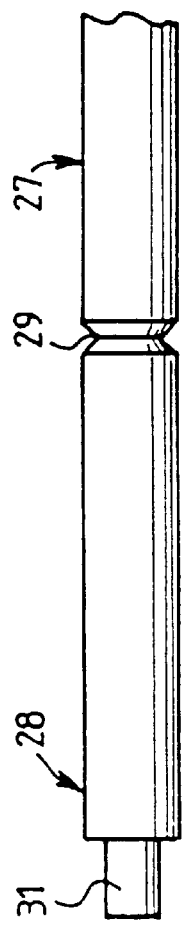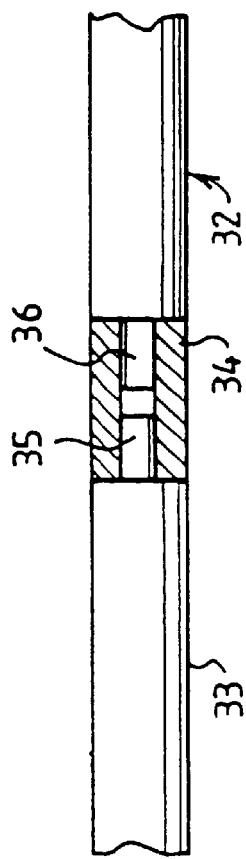

VERTEBRAL ROD FOR SPINAL OSTEOSYNTHESIS INSTRUMENTATION AND OSTEOSYNTHESIS INSTRUMENTATION, INCLUDING SAID ROD

BACKGROUND OF THE INVENTION

The present invention relates to a vertebral rod for a spinal osteosynthesis instrumentation, this rod having a constant diameter throughout its length and being adapted to receive bone anchorage implants, and to the osteosynthesis instrumentation including at least one of said rod.

In these instrumentations, the implants anchored in the bone (screws or hooks) have surfaces adapted to the diameter of the rod employed. In many instrumentations, the rods shaped to the anatomy of the vertebral segments on which they must be installed, remain rigid, as described in the French patent 83 07 450 (2 545 350).

However, in some cases, a variable stiffness may be found desirable, the vertebral rod being for example rigid in one part of its length and relatively flexible in the other part. Thus the European patent EP-A-0 612 507 describes a lumbo-sacral instrumentation comprising rods formed by a rigid part and a flexible terminal part which has a diameter less than that of the rigid part. This arrangement permits in this particular case overcoming the difficulties caused by the existence of a "neohinge" ("neocharniere") between the welded vertebrae and the first superjacent vertebra. This solution however requires the use of different implants for each of the two parts of the rod since these implants must indeed be adapted to different diameters of the rod, which involves additional constraints and cost.

SUMMARY OF THE INVENTION

An object of the invention is to provide a vertebral rod of variable stiffness with the same implants along the whole of the length of the rod, which avoids this drawback.

According to the invention, the vertebral rod, of constant diameter throughout its length, comprises means for varying its stiffness between its ends.

In one embodiment of the invention, said means comprise a bore formed axially in the rod and extending in at least a part of the length of the rod.

In this way, the stiffness of the portion of the rod in which the bore is formed is less than that of the solid portion, without this variation in stiffness modifying the diameter of the rod, which permits using the same implants on the parts of different stiffnesses. This affords a substantial advantage since only a single set of implants is required instead of two and any risk of errors in the choice of the implants is avoided.

In another embodiment, the bore has at least two axial regions of different cross sections.

If this bore only extends in a part of the length of the rod, the latter will then have at least three regions of different stiffness.

In another embodiment of the invention, the axial bore has a constant section, is filled with a metallic material and encased with a different metallic material.

The invention not only permits using the same implants with a rod having a constant section and a variable stiffness, but also permits avoiding the modification of the connection means between the implants and the rod, which was required with the rod of variable diameter disclosed in the aforementioned European patent.

The variation in the stiffness may be achieved by varying either the longitudinal section of the rod along its longitudinal axis, or the cross section of the rod in a radial plane, or by a choice of different materials in the case of an association of different materials Further features and advantages of the invention will appear in the course of the following description, with reference to the accompaying drawings which illustrate several embodiments by way of a non-limitative example.

BRIEF DESCRIPTION OF THE DRAWINGS

FIG. 1 is a longitudinal sectional view of a first embodiment of a vertebral rod according to the invention.

FIG. 2 is a graph representing the variation in the stiffness of the rod of FIG. 1 along its longitudinal axis.

FIGS. 3, 4 and 5 are cross-sectional views of three other embodiments of the rod according to the invention.

FIG. 10 is a longitudinal view, partly in elevation and partly in section, of a vertebral rod according to a ninth embodiment of the invention.

FIG. 11 is a longitudinal elevational view of a vertebral rod according to a tenth embodiment of the invention.

FIG. 12 is a longitudinal elevational view of a rod according to an eleventh embodiment.

DESCRIPTION OF THE PREFERRED EMBODIMENTS

Figure 6:
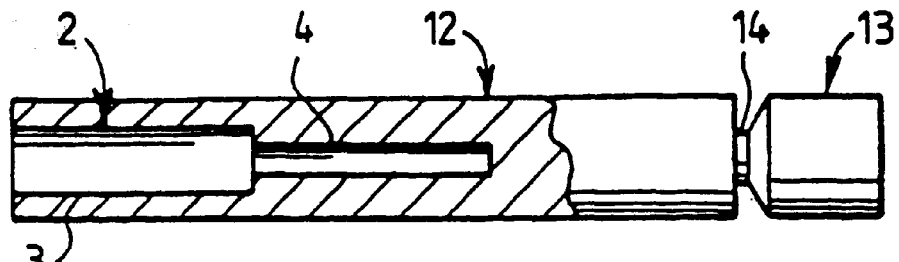
FIG. 6 is a longitudinal sectional view of a fifth embodiment of the rod according to the invention.

The vertebral rod 1 shown in FIG. 1 has a constant cross section throughout its length and is hollow in a part of its length: indeed, it has a axial bore 2 consisting of a first portion 3 having a diameter d1, and a second portion 4 having a diameter d2 less than d1. In this embodiment, the bore 2 extends along a part of the length of the rod 1 so that the rod has three longitudinal parts of different stiffness: a first part of maximum stiffness R1 corresponding to the solid section of the rod 1, a second part of stiffness R2 less than R1 corresponding to the portion 4 of the bore 2, and lastly a third part of stiffness R3 less than R2 corresponding to the portion 3 of diameter d1, the last portion opening onto the free end of the rod 1.

In the embodiment of FIG. 1, the stiffness varies along the longitudinal axis ZZ of the rod 1 by varying the cross section of the bore 2.

In the embodiments of FIGS. 3, 4 and 5, on the other hand, the stiffness varies in a radial plane about the radial axes XX and YY: the embodiment of FIG. 3 corresponds to a rod 5 having an axial bore 6 of circular cross section. The rod 7 of FIG. 4 comprises a bore 8 which is also of circular cross section but is radially offset from the longitudinal axis ZZ. Lastly, the rod 9 of FIG. 5 comprises a bore 11 whose surface extends around the longitudinal axis but has a non-circular, for example an oval or elliptic, cross section.

In the various embodiments of FIGS. 3, 4 and 5, the moments of inertia are different about the axes XX and YY, which results in a stiffness which differs according to the axis.

The rod 12 of FIG. 6 comprises an axial bore 2 similar to that of rod 1, but is provided at its end remote from the first part 3 of the bore 2, with a separable terminal member 13 having the same cross section as the rest of the rod 12. This terminal member 13 is connected to the rod 12 by a region 14 of reduced strength constituting a fracture initiator.

The terminal member 13 can be removed by bending or torsion with the aid of a suitable tool (not shown) after the rod 12 with the corresponding anchorage means (not shown) have been mounted on the spinal segment.

Owing to the fact that the terminal member 13 may be separated after the mounting of the instrumentation of which the rod 12 is a part, there is obtained after the vertebral correction, a rod whose length is shorter than at the beginning of the intervention, which is an important advantage in cases where the sufficient length of the rod at the end of the intervention is less than the required initial length. This is the case, for example, when restoring a physiological curvature after a surgical operation and ensuring that an end of the rod does not uselessly project, in particular when restoring a lumbar lordosis subsequent to an intervention on a degenerated element, i.e. a painful damaged vertebral disc.

Indeed, initially, the surgeon must in this case use a rectilinear rod of a certain length by means of which he produces a distraction, and then a compression accompanied by a bending of the rod. At the end of this compression and bending, one of the bone anchorage means has slid in the direction of the other and consequently uncovered a free end portion of the rod which becomes a hindrance.

This free end must then be eliminated in one way or another, and this may be easily accomplished without danger to the patient if it is formed by a detachable terminal member such as the terminal member 13 which can be broken off.

Figure 7:
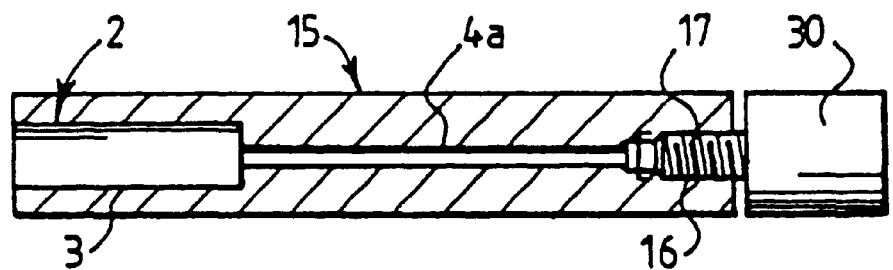
FIG. 7 is a longitudinal sectional view of a sixth embodiment of the rod according to the invention.

In the embodiment of FIG. 7, the rod 15 has an axial bore 2 comparable to that of FIG. 6, but the part 4a of this bore is extended by an axial tapped hole 16 which opens onto the free end of the rod 15. Screwed in the tapped hole 16 is a threaded spigot 17 which axially projects from a terminal member 30 of the same cross section as the rest of the rod 15 with which it forms one piece when the spigot 17 is screwed in the hole 16.

Figure 15:
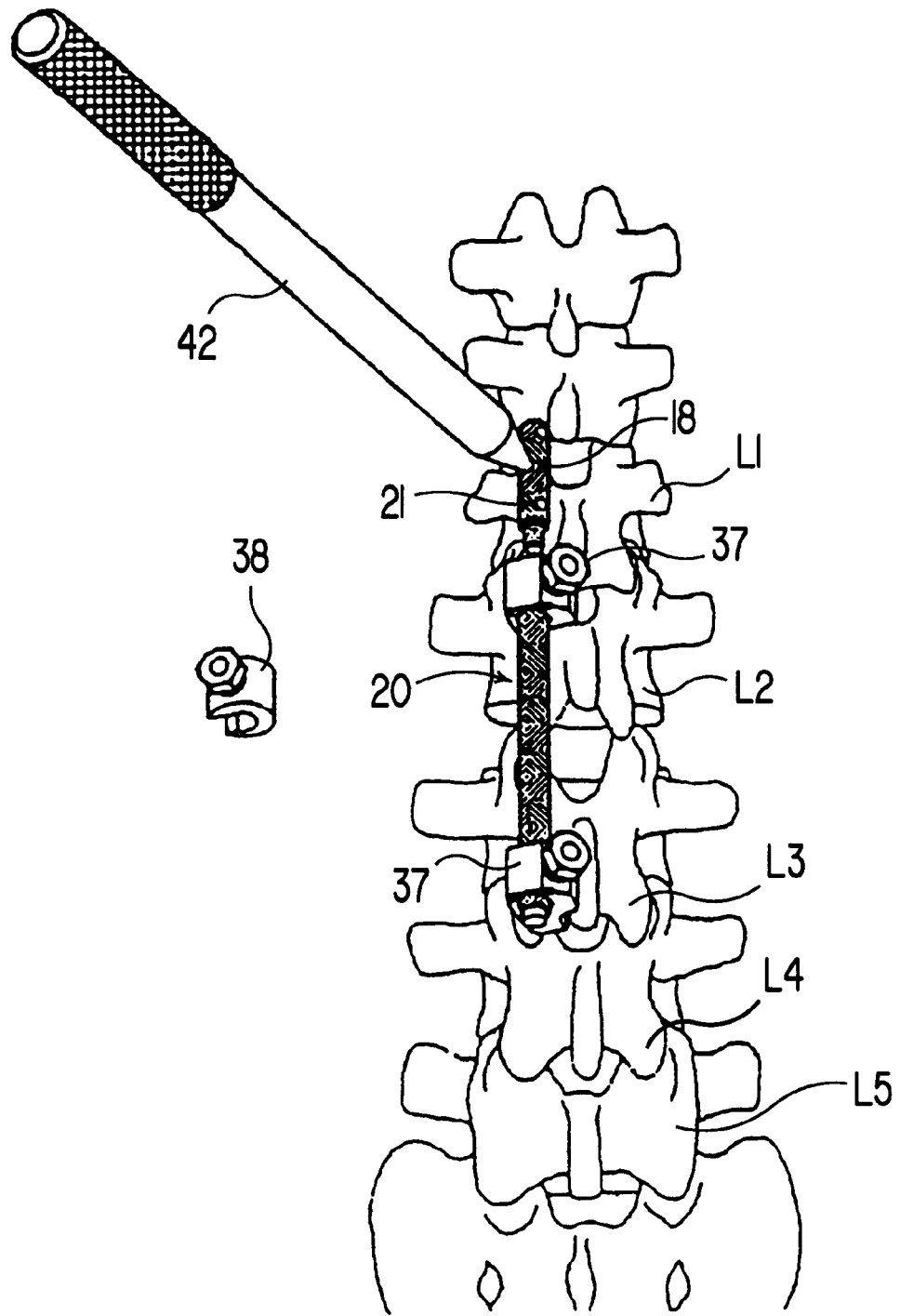

The terminal member 30 may be advantageously identical to the terminal member 18 of FIG. 10 and the rod 15 may have a surface with asperities, such as a knurled surface 19. The terminal member 18 may be unscrewed by hand after the instrumentation has been placed in position by the surgeon, for example by means of a knurling provided on the surface of the terminal member 18, or by means of a suitable unscrewing tool 42 whose end may be inserted in succession in openings 21 provided radially in the terminal member 18 (FIG. 15).

Figure 8:
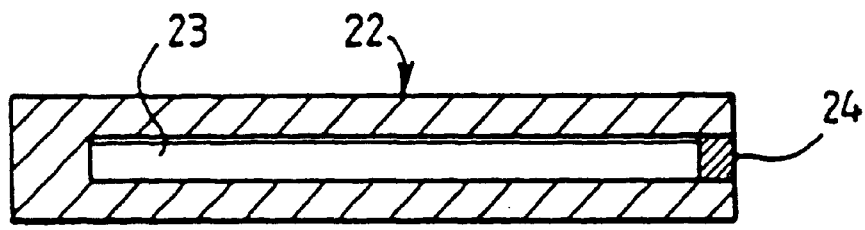
FIG. 8 is a longitudinal sectional view of a seventh embodiment of the rod according to the invention.

In the embodiment of FIG. 8, the rod 22 does not have a separable terminal member but an axial bore 23 of constant cross section extending along the major part of the length of the rod. At one of its ends, the bore 23 terminates in a closing member 24, for example a plug screwed in the end of the bore 23.

Figure 9:
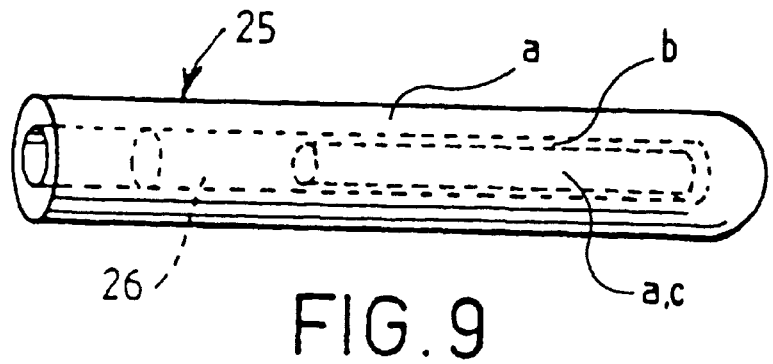
FIG. 9 is a perspective view of an eighth embodiment of the rod according to the invention.

In the embodiment of FIG. 9, the rod 25 comprises an axial bore extending along a part of its length and filled with a core 26, for example composed of a metal, the rest of the rod 25 being composed of a metallic material different from that of the core 26. The latter may also be formed of a plastics material or any other biocompatible material. In different cases, the core 26 has a stiffness different from that of the material constituting the rest of the rod 25 and extends only along a part of the length of this rod, which permits varying the stiffness along the longitudinal axis.

The rod 27 of FIG. 11 does not have an axial bore and is therefore solid throughout its length. This rod 27 is provided at one of its ends with a terminal member 28 which can be broken off and is connected to the end of the rod 27 by a region 29 of smaller section and consequently of reduced strength, constituting a fracture initiator. The terminal member 28 may be provided with torsion-bending means for breaking it off after the instrumentation including the rod 27 has been placed in position. In the embodiment illustrated in FIG. 11, these torsion means are formed by a shaped end portion 31 which projects from the end of the terminal member 28 remote from the fracture-initiator region 29. This shaped portion is for example of hexagonal cross section and is capable of receiving a corresponding driving tool (not shown). As a variant, the torsion means may be in the form of openings provided radially in the terminal member 28, such as the openings 21 of the terminal member 18 (FIG. 10).

In the embodiment illustrated in FIG. 12, the rod 32 is connected to a separable terminal member 33 by a cylindrical intermediate member 34 of the same outer diameter as the rods 32, 33 into which extend terminal spigots 35, 36 of the terminal member 33 and the rod 32 respectively. The member 34 is fixed to the spigots 35, 36 by any suitable means, known per se.

Figure 13:
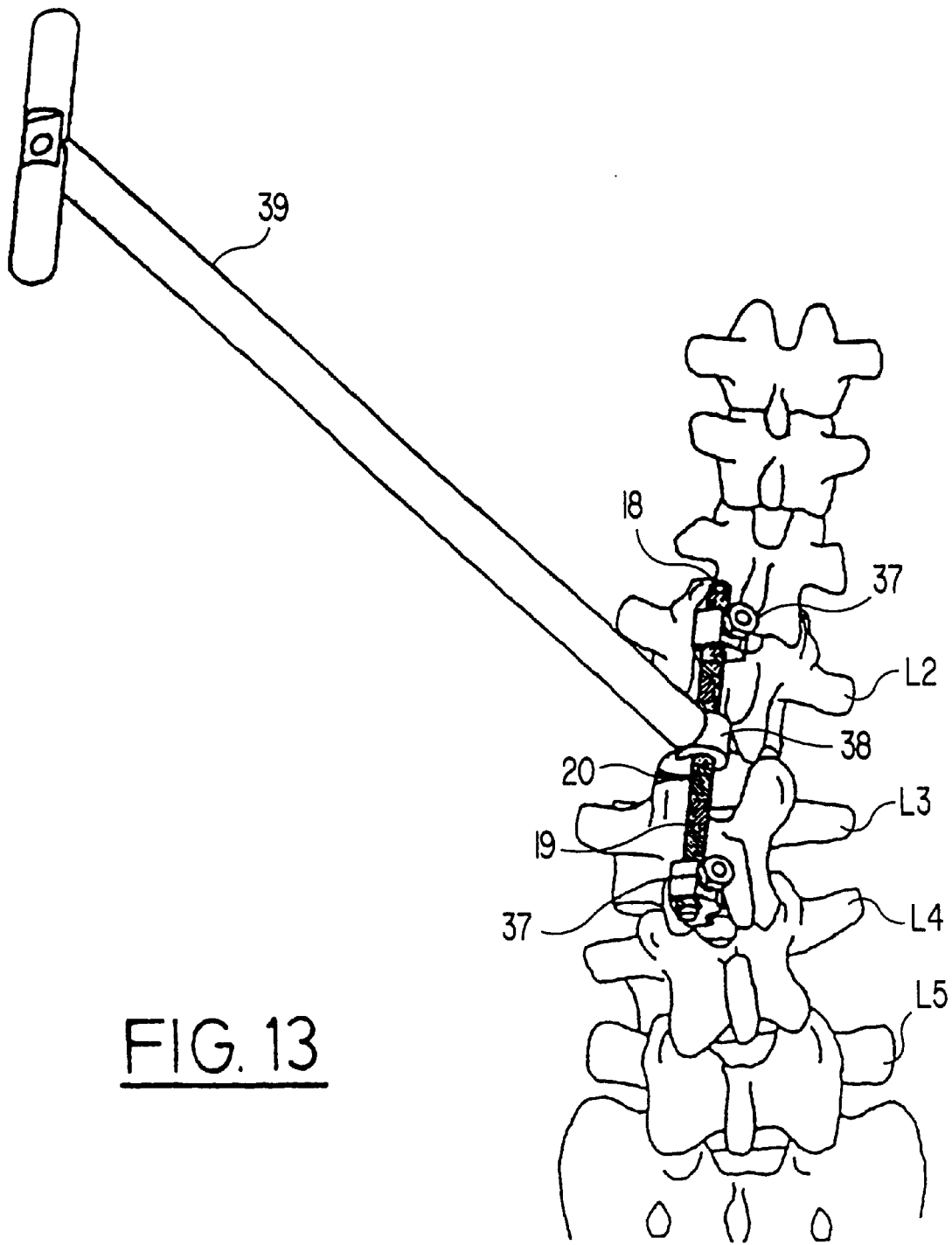
FIGS. 13, 14 and 15 illustrate steps in the placing in position of a rod according to FIG. 9 provided with corresponding bone anchorage implants on a vertebral segment by a surgeon.
Figure 14:
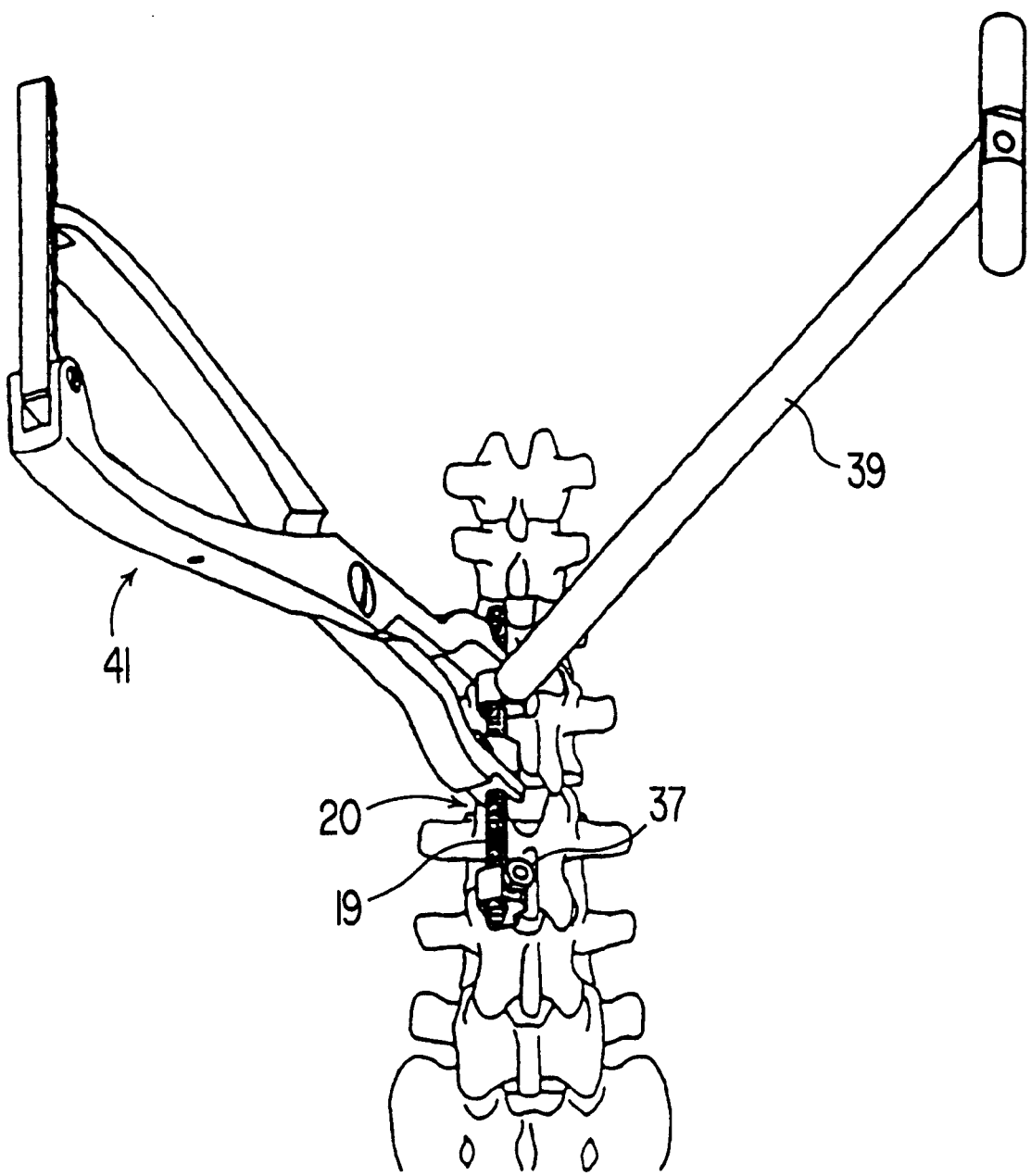

FIGS. 13, 14 and 15 illustrate a portion of a spine including lumbar vertebrae L1 through L5 and the steps in the mounting of a vertebral rod 20 provided with a screwed terminal member 18, on two lumbar vertebrae L3, L2 of a spine.

Mounted on the rod 20 are two anchorage implants 37 of known type (bone anchorage screw or hook). The surgeon temporalily places on the rectilinear rod 20 between the anchorage implants 37, a C-shaped collar 38 fixed to the end of the handle 39 of a tool. The lower anchorage implant 37 is fixed in position on the rod 20 and the upper anchorage implant 37 is allowed to slide along the rod.

In FIG. 14, the surgeon uses a pliers 41 for exerting along the axis of the rod 20, by bearing against the collar 38, a force of compression which causes a descent of the upper anchorage implant 37 and moves it toward the lower anchorage implant 37. At the end of this compression, the upper anchorage implant 37 is clamped on the rod 20 in a position short of the terminal member 18. The compression permits restoring for example the alignment of the spinal column.

In the last step (FIG. 15), a tool 42 is used for unscrewing the terminal member 18 and separating it from the rod 20 by inserting the point of the tool 42 in the successive openings 21 provided for this purpose on the terminal member 18. The collar 38 is removed from the rod 20. When the terminal member 18 has been removed, the anchorage means 37 are in position at both ends of the rod without any part of the latter projecting from the anchorage means 37 and without the removal of the terminal member 18 involving any risk for the patient.

The invention is not limited to the various described embodiments and may include many alternative embodiments. For example, the rod 20 may be either solid, as shown in FIG. 10, or provided with an axial bore according to any one of the embodiments of FIGS. 1 to 9. It will be clear that the same is true of the rods 27 and 32. The bore 26 can be filled with a metallic material, biocompatible or not, and embedded within a biocompatible plastic material. Similarly, the rod would be constituted in at least three layers designed in at least two different materials, for example according to distribution a-b-a or a-b-c.

What is claimed is:

1. A spinal fixation system, comprising:

a rod formed of a first material and defining a passage extending at least partially therethrough, said passage being at least partially filled with a second material different from said first material to vary the stiffness of said rod; and a number of bone anchorage implants, said implants each including a fastener for selective fixation to said rod.

2. The system of claim 1 wherein said first material has a stiffness different from said second material.

3. The system of claim 1 wherein at least one of said first material and said second material is metallic.

4. The system of claim 1 wherein one of said first material and said second material includes a plastic.

5. The system of claim 1 wherein said first material includes a first metal, and wherein said second material includes a second metal having a stiffness different from said first metal.

6. The system of claim 1 wherein said first material includes a first metal, and wherein said second material includes a plastic having a stiffness different from said first metal.

7. The system of claim 1 wherein said rod is formed of at least three layers, at least one of said layers being formed from a different material than another of said layers.

8. The system of claim 1 wherein said rod has a generally uniform outer cross section, and wherein said passage has a uniform, circular cross section.

9. The system of claim 1 wherein said passage has a non-circular cross section.

10. The system of claim 1 wherein said passage has at least two regions defining different cross sections.

11. A spinal fixation system, comprising:

a rod defining a longitudinal central axis and a passage extending at least partially therethrough in a longitudinal direction, said passage being radially offset from said axis to vary stiffness of said rod; and a number bone anchorage implants, said implants each including a fastener for selective fixation to said rod.

12. The system of claim 11 wherein said rod has a generally uniform outer cross section, and wherein said passage has a generally uniform, circular cross section.

13. The system of claim 12 wherein said passage has a non-circular cross section.

14. The system of claim 13 wherein said passage has a generally elliptical cross section.

15. The system of claim 11 wherein said passage has at least two regions defining different cross sections.

16. A spinal fixation system, comprising:

a rod having a longitudinal axis and defining a passage along only a part of its length, the rod being formed from a metallic material and the passage being at least partially filled with a core material having a stiffness different than the metallic material to correspondingly vary stiffness along the longitudinal axis.

17. The system of claim 16, further comprising a number of bone anchorage implants, each including a fastener operable to connect said rod to a patient's spine.

18. The system of claim 16 wherein said core material is a metal.

19. The system of claim 16 wherein said core material is a plastic.

20. The system of claim 16 wherein said rod has a generally uniform outer cross section.

* * * * *